(12) United States Patent
Rasmussen et al.

(10) Patent No.: US 7,383,838 B2
(45) Date of Patent: Jun. 10, 2008

(54) MECHANICAL RETURN BLOCKING DEVICE

(75) Inventors: Jørgen Rasmussen, Struer (DK); Søren Christrup, Struer (DK)

(73) Assignee: Bang & Olufsen Medicom A/S, Struer (DK)

( * ) Notice: Subject to any disclaimer, the term of this patent is extended or adjusted under 35 U.S.C. 154(b) by 197 days.

(21) Appl. No.: 10/564,430

(22) PCT Filed: Jul. 9, 2004

(86) PCT No.: PCT/DK2004/000499

§ 371 (c)(1),
(2), (4) Date: Feb. 3, 2006

(87) PCT Pub. No.: WO2005/004960

PCT Pub. Date: Jan. 20, 2005

(65) Prior Publication Data

US 2006/0290145 A1    Dec. 28, 2006

(30) Foreign Application Priority Data

Jul. 11, 2003   (DK) ................................ 2003 01054

(51) Int. Cl.
*A61M 11/00* (2006.01)

(52) U.S. Cl. ............................. 128/203.12; 128/205.24

(58) Field of Classification Search ........... 128/203.12, 128/200.23, 205.24, 207.16, 200.24
See application file for complete search history.

(56) References Cited

U.S. PATENT DOCUMENTS

| 2,129,412 A | 9/1938 | Edele |
| 2002/0157666 A1 | 10/2002 | Ferris |

FOREIGN PATENT DOCUMENTS

| CH | 267906 | 7/1950 |
| DE | 149926 | 10/1902 |
| EP | 0959211 | 11/1999 |
| FR | 2169664 | 7/1973 |
| FR | 2288844 | 5/1976 |
| FR | 2373658 | 7/1978 |
| WO | WO 2004/041334 | 5/2004 |

*Primary Examiner*—Steven O. Douglas
(74) *Attorney, Agent, or Firm*—James Creighton Wray; Clifford D. Hyra

(57) ABSTRACT

It is an object of the present invention to provide a mechanical blocking device by means of which the user will only be able to initiate an event by activating a stroke of the button or lever past the activation point of the event. Should the movement of the button or lever be stopped or the direction changed before reaching the activation point, retaining means will hinder further movement in the first direction before the lever or button has been brought back to its starting position.

14 Claims, 5 Drawing Sheets

MECHANICAL RETURN BLOCKING DEVICE

This application claims the benefit of Danish Application No. PA 2003 01054 filed Jul. 11, 2003 and PCT/DK2004/000499 filed Jul. 9, 2004, which are hereby incorporated by reference in their entirety.

BACKGROUND OF THE INVENTION

The present invention relates to a mechanical return blocking device and further a device where such a mechanical return blocking device is incorporated.

Return blocking devices may be used for a multitude of purposes.

An example of a return blocking device for maintaining a window or door in an open position is known from U.S. Pat. No. 2,129,412. In particular in the second embodiment of this document, a return blocking device is described where a ratchet is arranged inside a housing. Through a slit in the housing, a second movable member is inserted. The movable member comprises an engagement section which is adapted for engagement with the ratchet. As the second member moves in a first direction, counter movement will be hindered by the triangular shape of the ratchet. When the second member comes to the end of the ratchet, it will, due to the influence of a spring, be pushed downwards, whereby travel is allowed in the opposite direction under the ratchet. Due to the further provision of a second spring member, the second member will be guided upwards towards the beginning of the ratchet such that forward movement may be possible again. This construction comprises a number of drawbacks, for example the entire construction is placed in a housing, whereby debris or other foreign objects stuck inside the housing eventually will hamper the proper working of the device. For example, if foreign matter has become wedged between the second spring device and the bottom of the device, it will not be possible to push the engagement section back up on the second track. Furthermore, foreign matter stuck under the ratchet, i.e. between the second track and the first track, will likewise hinder the proper functioning of the device. Also, as it is evident from further embodiments of the present invention, this device does not allow for the movable member to return to the first position halfway through the ratchet, but needs to continue all the way to the end in order to fall down to the first track provided underneath the ratchet in order to travel backwards to the original beginning position. Furthermore, the proper workings of the device is wholly dependent on the ability of the second spring member to force the engagement section back up at the level of the ratchet means, otherwise the device will be completely useless.

From the prior art document FR 2169664 is known a device for use in order to maintain a window in a more or less open position in relation to a frame. The device comprises two co-axially arranged and mutually displaceable arm parts as well as a locking member which is pivotally and biasly arranged in the outer member of the two co-axially arranged members such that a notch on the locking member may engage a centrally located displaceable member. The locking notch will travel on inclined surfaces and will be guided from one track to the opposite track on the inclined surfaces in relation to different retaining possibilities arranged on the interior member along the locking members' travel. In order to allow movement, the pivotal locking member must be pivoted manually onto one or the other track in order to decide whether the window shall be more or less open.

In a further embodiment in this prior art invention, the locking member is provided with a spring biasing means such that accidental relative movement of the two co-axially arranged parts does not cause the window to move in relation to the frame without actively and forcefully bringing the locking member out of engagement with the co-axially internal member.

It is, therefore, an object of the present invention to provide a mechanical return blocking device which alleviates these disadvantages, and at the same time provides a number of further advantages, which provides for a wide range of applications, wherein the device according to U.S. Pat. No. 2,129,412 would not be considered suitable.

In a number of applications a certain task is performed or carried out by manually depressing a button or lever, which in turn causes one or more events to happen.

In a number of these applications it is desirable to assure that either a stroke of the button or lever has been performed or at least that the stroke of the button or lever was sufficient in order to activate the event in question.

Below as an example of devices where this situation is important will be discussed an example relating to an asthma inhalation device.

These types of asthma inhalation devices function in a way whereby the user/patient when needing to inhale the medication places the asthma inhalation device with a mouthpiece in the patient's mouth and thereafter activates a button. By depressing the button a canister inside the device is activated such that a medication dose stored in the valve system in the canister is dispensed through the mouthpiece to the patient.

Often these types of devices comprise a dose counter such that the patient will be able to keep track of how many doses are left in the device such that a new device or canister can be provided in due time. It is therefore important that when the patient dispenses a dose, only one dose is dispensed and at the same time only one dose is counted.

Due to inherent tolerances in production in order to keep production costs of these types of devices as low as possible, and furthermore as a consequence of the play arising from a number of mutually cooperating parts, it is sometimes possible to activate the bottom either from the non-depressed state or from the semi-depressed state, whereby the dose counter may be activated without an actual dose being dispensed or a dose may be dispensed without activating the dose counter.

For this type of device as for many other types of devices it is undesirable that depression of a button/lever, which is intended to effect a function, i.e. initiate an event, where said function may have more than one result, i.e. the example mentioned above, the activation of the button shall result in the dispensation of a dose and at the same time counting/registration of said dose. It is paramount that both these events happening by depressing the bottom are reliable registered and carried out without the possibility of unintended or intended tampering with the device.

SUMMARY OF THE INVENTION

It is therefore also an object of the present invention to provide a mechanical blocking device by means of which the user will only be able to activate an event by a stroke of the button or lever such that the event or events intended to be activated by depressing the button/lever will reliably be carried out and/or registered at the same time, or in a synchronised manner.

Consequently the present invention provides a mechanical return blocking device comprising two cooperating and mutually displaceable parts:

a first part wherein parallel to a longitudinal axis at least one set of tracks comprising a first track and a second track is provided, and that the second track comprises one or more retaining members and a sliding guide ranged at one end of the second track;

a second cooperating part wherein a leg member comprising an engagement section for engagement with the tracks provided on the first part is provided, and that said leg member is biased towards the first part and that the engagement section is adapted to travel in the direction of the longitudinal axis;

and further that the retaining members allows the engagement section of the leg member to move in a first direction towards the sliding guide but blocks movement in the opposite second direction and that the engagement section of the leg member after having passed the sliding guide moving in the first direction, and the travel direction is reversed, slides on the sliding guide, whereby the engagement section and thereby the leg member is directed from the second track to the first track for unhindered movement on said first track in said second direction.

The device thereby provides a first track where the engagement means can travel unhindered in one direction. When built into a device where it is desirable to have a complete button stroke, the engagement section will slide on the first track completely unhindered. During the movement in the first direction the engagement section of the leg member will abut the side of the second track made up of one or more retaining members due to the biasing force applied to the engagement section. Once the engagement section reaches the bottom of the intended travelling stroke corresponding to a stroke of the button/lever, the biasing force will push the engagement section onto the second track and the engagement section will move in a second direction towards its starting position and thereby pass the one or more retaining members.

Should a user during the movement in the second direction of the engagement means alter the direction, i.e. try to depress the button/lever again, the engagement section will engage the retaining members, whereby relative movement of the two cooperating parts will be impossible.

Should a user during the depressing of a button corresponding to the engagement section moving in the first track change direction, i.e. from first to second direction, such that the engagement section begins a movement in the opposite direction, the biasing force will urge the engagement section onto the second track such that further forward movement will be hindered by the engagement section's position in the second track where one or more retaining members are provided, whereby further movement in the first direction is impossible.

In order to again move the engagement section in the first direction corresponding to pushing/activating the button or lever again, the engagement section must have been returned and the engagement section must have been brought into contact with the sliding guide, whereby the engagement section during a further forward movement again will slide in the first track abutting the retaining members on the way to completing an activation of the event by the button/lever.

In this manner by designing the one or more retaining members in such a way that the event which should be triggered by activating the button/lever will only take place once one or more of the retaining members have been passed in the first direction, it can be assured that a reliable action when depressing the button/lever is facilitated. If a depression of the button/lever is disengaged during the travel, the engagement section as described above will be forced into the second track and will by further movement in the first direction engage the retaining members making travelling in that direction impossible.

Therefore by arranging retaining members correctly, play in the device and tolerances can be counteracted, whereas a movement of the button/lever for activation or initiating of the event will reliably be carried out by the device. Tolerances and play in the device are therefore assimilated by the initial movement of the engagement section in the first track and once it enters the activation zone, it is due to the construction of the device impossible to turn back and reactivate without a complete return to the starting position. This in turn means that the activation should be provided for by a relatively short movement of the button/lever.

In a further advantageous embodiment each retaining member comprises an inclined sliding surface having a predetermined length along which the engagement section will slide, and a step in the shape of a surface arranged at a sharp angle in relation to the sliding surface, said step connecting the top of one inclined sliding surface and the bottom of the next sliding surface, such that a saw-tooth configuration is created, and such that the engagement section of the leg will be retained from movement in one direction by said step.

This configuration is relatively simple to produce and further the construction can be made such that a user will feel the teeth of the saw tooth structure indicating that the button is in its return movement. When constructing the device itself it is relatively simple to design the length of the sliding surface such that it will be designed exactly for the desired movement of the button/lever.

The formulation "step in the shape of a surface arranged at a sharp angle in relation to the sliding surface" shall in this context and within the application be understood as a surface at such an angle that the engagement section of the leg member travelling up the inclined sliding surface, will fall down and be retained by this step, which thereby hinders the movement in one direction and therefore only allows the engagement section to travel up the adjacent sliding surface if such is provided.

In a further advantageous embodiment at least a part of a side surface facing the first track of each retaining member is arranged at a shallow angle in respect to the longitudinal axis of the device, such that the inclined sliding surface is narrowest in the end of the forward travelling direction of the engagement section.

In this embodiment it is provided that the side surface of the second track, against which the engagement means abuts by movement in the first direction, is made such that the engagement means will not become stuck due to unevenness or the like in that by arranging the side of the retaining member at a shallow angle, the engagement member which abuts this side will continuously be pushed outwards during its movement in the track.

In a further advantageous embodiment the inclined sliding surface overlaps an adjacent inclined sliding surface, and the inclined sliding surface tapers perpendicular to the longitudinal axis such that the top is narrower than the bottom of the sliding surface, whereby the step at the bottom is narrower than the adjacent sliding surface at their connection point.

By this construction a wedge-shaped part of the inclined sliding surface is exposed next to the adjacent retaining means. During the reverse movement where the engagement section moves into engagement with the retaining means, the wedge-shaped section exposed by the taping side section facilitates the engagement sections travel into the retaining means.

In a still further advantageous embodiment the leg member is pivotally fastened in the end opposite the engagement section, and that the first part comprising the at least one set of tracks has a corresponding circular configuration arranged at a distance, whereby the engagement section may engage the tracks.

It is obvious that the device described above will function where the relative movements between the first and second parts are linear. It is however also contemplated within the scope of the invention that the leg member can be pivotally fastened such that the engagement section will perform a movement corresponding to a partly circular movement. In order to contain the retaining means at a distance from the engagement section of the leg, the retaining means may also be arranged on a circular shaped member, where the radius of the circle corresponds to the distance between the pivotal fastening point of the leg member and the engagement section's outer tip. By this arrangement it is assured that when the activation of the lever or button translating the action to the leg, the engagement section of the leg will stay in abutting contact with the two tracks arranged on the first part. In this manner the same advantages are achieved as described above.

In a further embodiment the width of the sliding guide perpendicular to the longitudinal axis at its widest section is at least as wide as the retaining members step.

In a still further embodiment all parts of the device are made from a plastic material, preferably a mouldable material, and still further by an injection moulding process.

The choice of material will always depend on the application into which the device is to be built. With the material characteristics of plastic materials, especially most plastics providing for flexibility, light weight and relatively good strength, plastics is a preferred material in that the biasing properties of the leg can be cast into the leg itself and does not have to be provided by a different member such as a separate resilient member or a spring. Furthermore plastic and especially done by an injection moulding process is a cheap and reliable way of mass-producing items on a larger scale.

In a still further advantageous embodiment of the invention one or both of the mutually displaceable parts are relatively biased, for example by spring means, such that when the device is not operating the engagement means will be engaging a point on the sliding guide.

By constantly biasing one member in one direction it can be assured that the device rest situation will be where the leg member is ready to move into the first direction, i.e. slide along in abutting side contact with the retaining means. This may also be combined with the button or lever's zero position, i.e. the position wherefrom a stroke is to be commenced.

Although the mechanically blocking device according to the invention can be adapted to a number of different devices, a device such as a manually operated inhalation device is disclosed in an advantageous embodiment of the invention in which the dispensation of a medicament dose from a canister arranged in the device is activated by depressing a button or lever, which button or lever is further connected to a mechanically return blocking device where said device comprises two cooperating and mutually displaceable parts:

a first part wherein parallel to a longitudinal axis at least one set of tracks comprising a first track and a second track is provided, and that the second track comprises one or more retaining members and a sliding guide arranged at one end of the second track;

a second cooperating part wherein a leg member comprising an engagement section for engagement with the tracks provided on the first part is provided, and that said leg member is biased towards the first part and that the engagement section is adapted to travel in the direction of the longitudinal axis;

and further that the retaining members allows the engagement section of the leg member to move in a first direction towards the sliding guide but blocks movement in the opposite second direction and that the engagement section of the leg member slides on the sliding guide, whereby the engagement section and thereby the leg member is directed from the second track to the first track.

By incorporating the mechanical return blocking device into devices of this type and designing the size and distribution of the retaining members according to the use, it can be achieved that once a user activates the button or lever and moves it past the activation point, a dose is dispensed and also optionally a dose counting device is activated without the user being able to change direction. A change of direction necessitates that the button/lever is brought back to its initial starting position before a new stroke may be commenced.

In a further advantageous embodiment of the device the mutually displaceable parts are formed as integral parts of the device, such that the first or second part is integral with part of the button arrangement and the other part is integral with a non moving part of the device.

This manner of production facilitates that the inventive advantages of the device are provided at very low costs in that the parts of the device can be moulded from the outset with the two parts necessary in order to create the mechanical blocking device. Furthermore in cases where the device is injection moulded, it is a very simple and thereby cheap process to manufacture these added advantages into the device itself in that only the injection moulding tool has to be modified.

In a further advantageous embodiment the mechanical return blocking device is especially designed such that play and tolerances arising in the device from production, assembly and manufacturing circumstances are compensated by shaping and designing the engagement sections' travel between at least two adjacent retaining means or the retaining means and the sliding guide corresponds to the activation of one event, where an event may be the dispensation of a medicament dose and/or the input for a dose counting device.

By designing the device such that the event will take place only after the engagement section has past the last retaining means in the first track, it can be assured that depression of the button/lever either will not be completed and therefore the dose dispensation and dose counting will not be activated, or the button/lever is depressed all the way past the activation point or points in one movement assuring the correct dispensation and counting of a medicament dose.

Although the device has been described with respect to an inhalation device, the principle of assuring complete depression of a button or at least depression of a button so far that it is assured that the event which is desirable to happen upon depressing said button is achieved. This principle can of course be adapted and implemented in a number of devices where similar considerations relating to the stroke of the button/lever are appropriate.

The invention will now be explained with reference to the accompanying drawings, wherein

DETAILED DESCRIPTION OF THE PREFERRED EMBODIMENTS

Figure 1:
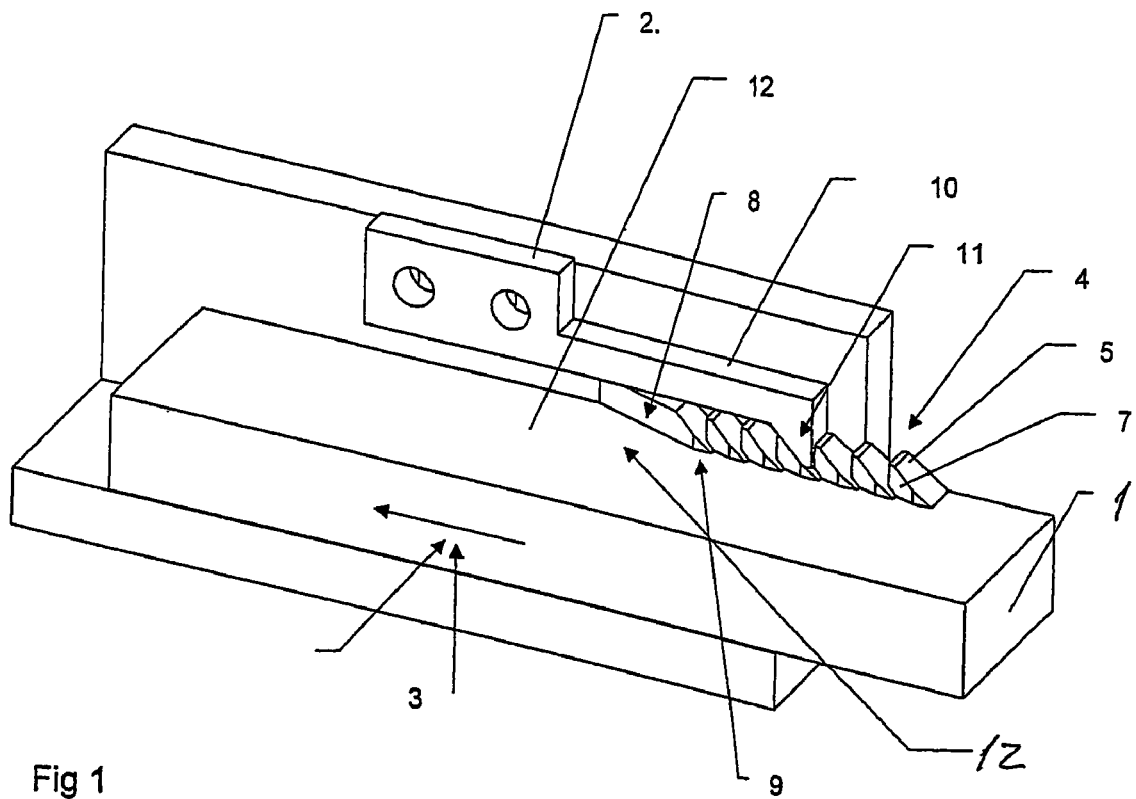
FIG. 1 illustrates an isometric view of the invention.

In FIG. 1 is illustrated two cooperating parts, a first part 1 and a second part 2. The two parts 1,2 are intended to be mutually displaceable such that the first part 1 will be able to slide in a first direction indicated by the arrow 3 in relation to the second part 2.

Which part slides in relation to which other part does not influence the proper workings of the device.

Figure 2:
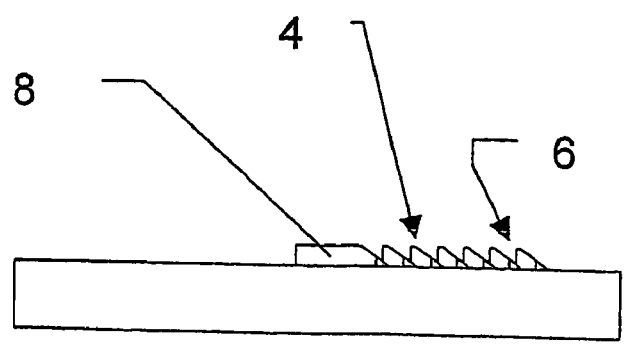
FIGS. 2, 3 and 4 illustrate different views of a first part.
Figure 3:
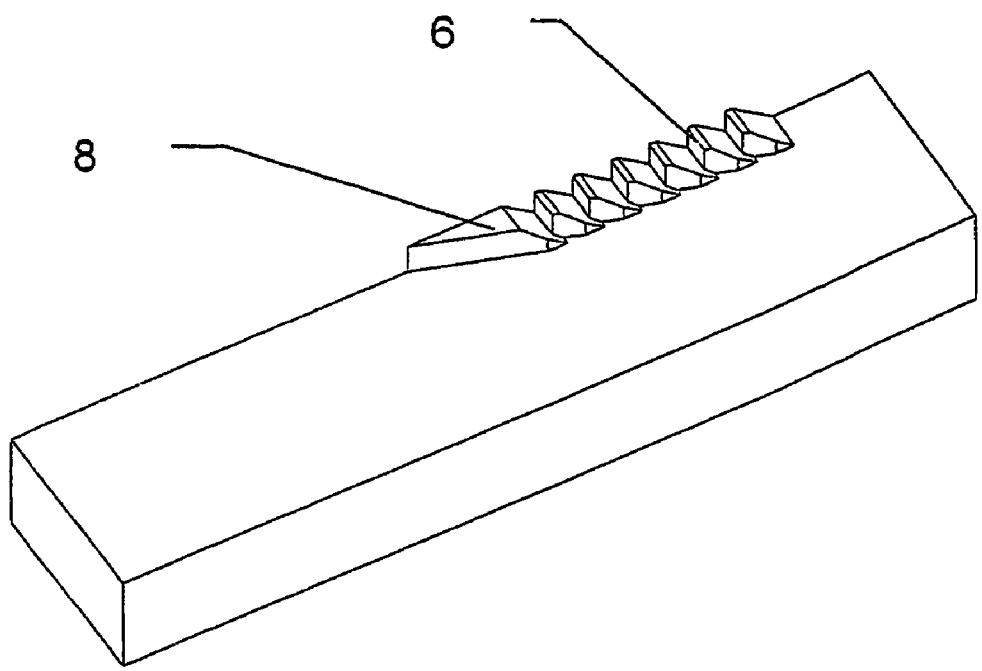

On the first part 1 is provided a number of retaining means 4, where each retaining means in the illustrated embodiment comprises an inclined sliding surface 5, which is connected with a step 6, see FIGS. 2 and 3. The step connects the top of one inclined surface 5 with the bottom of an adjacent inclined surface arranged on an adjacent retaining means. The retaining means is furthermore provided with a tapered surface 7.

Foremost in front of the retaining means 4 is arranged a sliding guide 8. The sliding guide tapers in the first direction such that the rear end 9 of the sliding guide will have the same width in a direction perpendicular to the first direction as indicated by the arrow 3 as the width of the inclined surface 5, whereas the taper brings the width to near 0. This tapered sliding guide can be seen more clearly in FIG. 3.

The second part 2 comprises a leg 10, which is biased toward the first part 1 such that an engagement section 11 may engage the retaining means 4.

As the two parts 1,2 are mutually displaced, for example from the position illustrated in FIG. 1, the engagement section 11 can only move to the left in relation to the first part in that the retaining means 4 will hinder any movement of the engagement section and thereby the second part to the right. As the engagement section comes to the end of the sliding guide 8, the engagement section will be guided onto the first track illustrated by the plane surface 12. In the illustrated example the second track is made up of the row of retaining members 4.

As the engagement means 11 are engaged toward the tracks, i.e. the row of retaining means 4 and surface 12, the engagement means will slide on the surface 12 when the first part 1 is moved to the left in relation to the leg member 10. Due to the biasing of the leg member 10, engagement section 11 will abut the side surfaces 9 of the retaining means. If the relative movement of the two sections is stopped and the direction altered, the engagement section 11 will slide up the exposed part of the inclined surface on the retaining means and the engagement section will slide into a position equivalent to the one illustrated in FIG. 1, whereby further movement to the right becomes impossible.

If, however, the relative movement of the two members 1,2 is continued from the start, i.e. from the end of the sliding guide 8 on the second track to the first inclined surface at the opposed end of the sliding track, the entire movement can be completed without any hindrance from the retaining means 4. On the return journey the engagement means will slide over the row of retaining means 4 until it reaches the sliding guide 8, whereby access to the first track will be free again for the engagement means.

Figure 4:
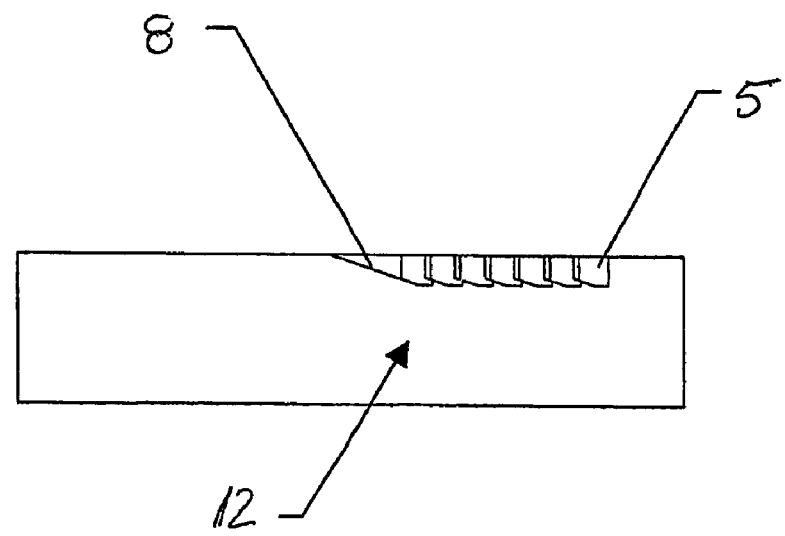

In FIG. 2-4 a cross-section through the second track is illustrated where the retaining means 4 are shown in a saw tooth embodiment.

Figure 5:
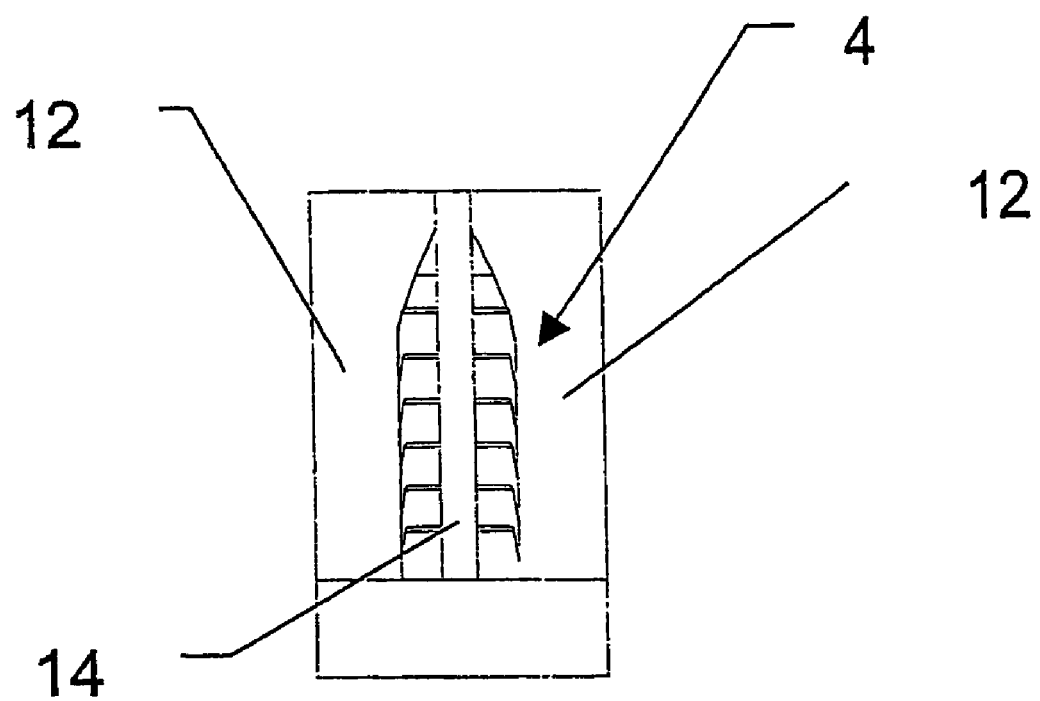
FIGS. 5 and 6 illustrate a curved embodiment of a first part.
Figure 6:
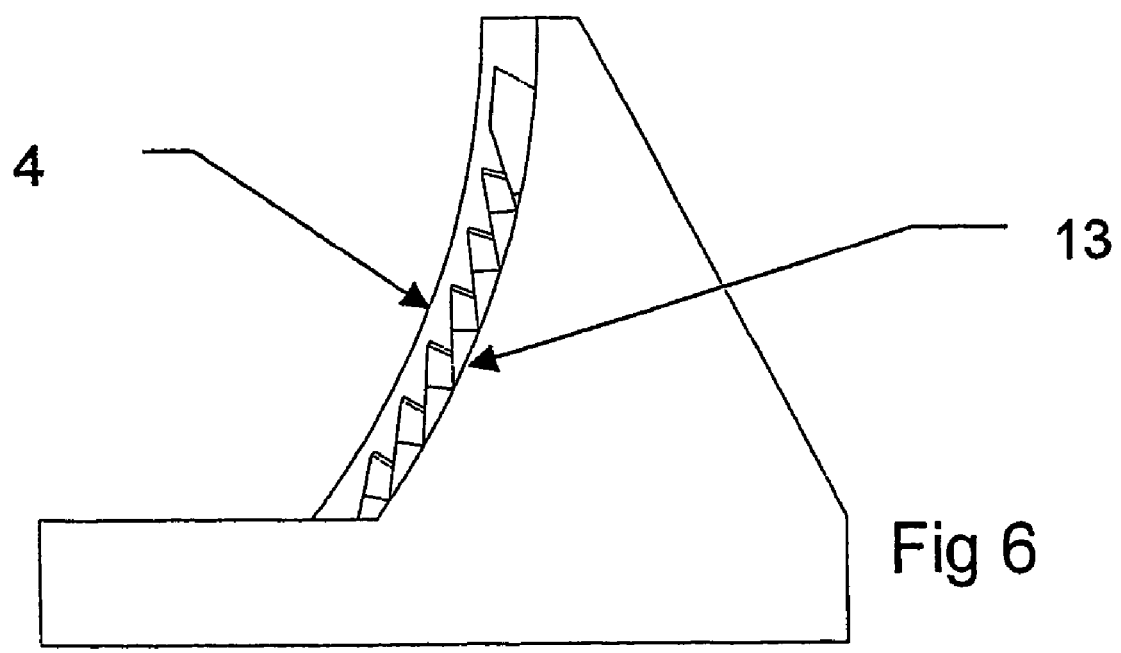

In FIGS. 5 and 6 an embodiment is illustrated where the retaining means 4 is arranged on a part of a circular member 13. When the leg 10 is arranged to pivot about a point as illustrated for example in FIG. 10, the engagement section 11 of the leg will describe part of a circle during its movement. By arranging the retaining means 4 on a circular member 13, where the distance between the pivot point and the circular member 13 is kept constant, the mechanical blocking device will function in a manner completely analogue to the one described with respect to FIG. 1.

In FIG. 5 is furthermore illustrated an embodiment where two parallel sets of two tracks are provided. In this embodiment a central divide 14 maintains the legs 10, not illustrated in FIG. 6, on respective separate sets of tracks on either side of the central divide 14.

In some embodiments it might be advantageous to be able to absorb larger forces and in such instances where it is not possible to enlarge the size of the members, additional sets of retaining means 4 and first tracks 12 can be provided to cooperate with a double set of legs.

Figure 7:
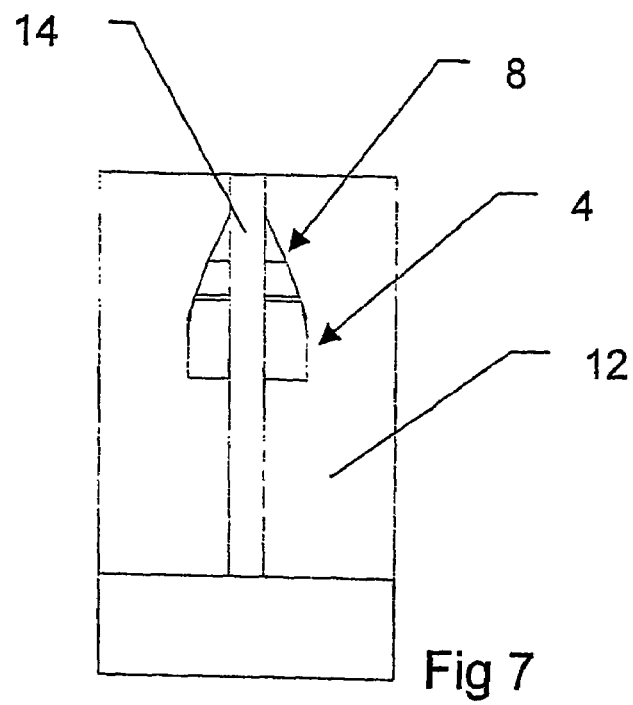
FIGS. 7, 8 and 9 illustrate a special embodiment comprising one retaining member.
Figure 8:
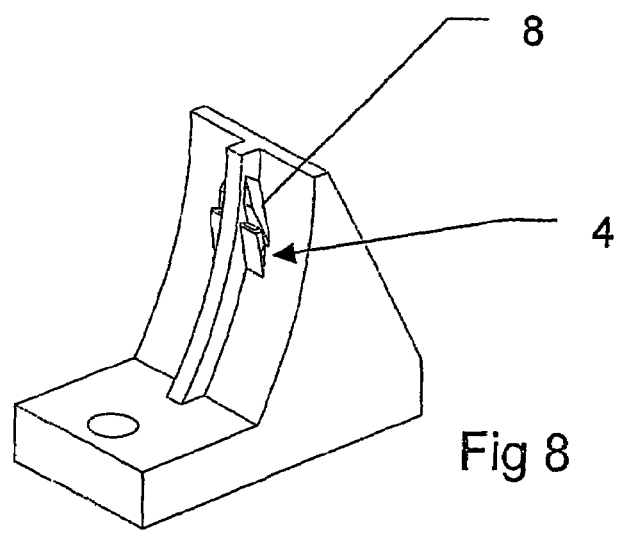
Figure 9:
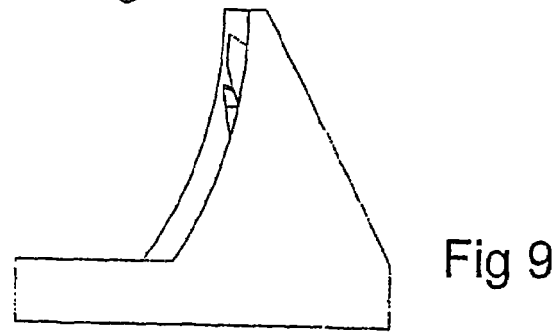

In FIGS. 7, 8 and 9 a special configuration of the invention is illustrated. In this configuration the mechanical blocking device is equipped with one retaining means 4 and one sliding ramp 8. This embodiment functions in exactly the same way as described above and is especially intended for cases where the construction shall insure that one event definitely takes place. The embodiment may be made as illustrated with two sets of tracks on either side of the middle divide 14, but may also be manufactured with only a single retaining means and a single sliding guide and a first track 12.

Figure 10:
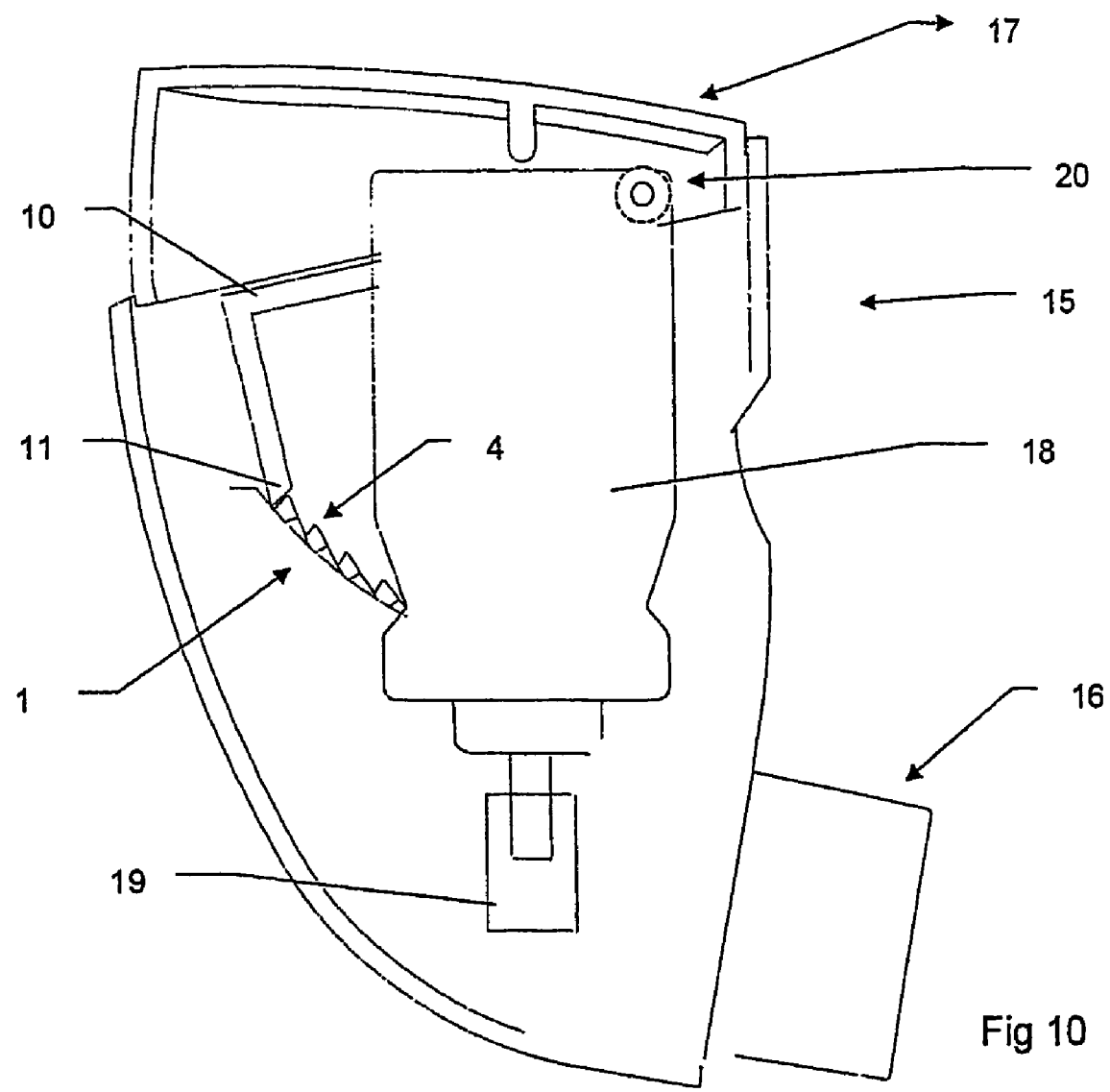
FIG. 10 illustrates a device comprising a mechanical blocking device.

Turning to FIG. 10 the mechanical return blocking device is illustrated as being built into an inhalation device 15.

A typical inhalation device comprises a mouthpiece 16, an activating button 17, a canister 18 comprising the medication to be dispensed through the mouthpiece 16. By depressing the button 17, the canister 18 will be forced downwards and via a valve device 19 a dose will be dispensed through the mouthpiece. In this embodiment the mechanical return blocking device is arranged such that the leg 10 is integrated in the button 17. The button 17 is designed to pivot about the pivot point 20. By this movement the engagement section 11 of the second part will abut the first part 1 which is integral with the inhalation device.

As described with reference to FIG. 1 the integrated mechanical return blocking device as illustrated in FIG. 10 operates in exactly the same manner, i.e. the engagement section 11 will move along the circular first part 1 and according to the movement either abut the side of the retaining means 4 or engage these, depending on the movement.

Although the device is described with reference to an inhalation device, it will be obvious that the principle of the mechanical return blocking device can be built into other devices, where a similar return blocking effect is desirable.

Also the retaining means has been discussed with reference to a saw tooth configuration as illustrated in FIG. 1, but retaining means being V-shaped cams or mutually circulating discs, which engage a retaining member in a non-stepwise manner may be contemplated within the scope of the present invention.

The invention claim is:

1. A mechanical return blocking device comprising two cooperating and mutually displaceable parts:
    a first part wherein parallel to a longitudinal axis at least one set of tracks comprising a first track and a second track is provided, and that the second track comprises one or more retaining members and a sliding guide arranged at one end of the second track;
    a second cooperating part wherein a leg member comprising an engagement section for engagement with the tracks provided on the first part is provided, and that said leg member is biased towards the first part and that the engagement section is adapted to travel in the direction of the longitudinal axis;
    and further that the retaining members allows the engagement section of the leg member to move unhindered in a first direction on said second track towards the sliding guide but blocks movement in an opposite second direction and that the engagement section of the leg member after having passed the sliding guide moving in the first direction, and the travel direction is reversed, slides on the sliding guide, whereby the engagement section and thereby the leg member is directed from the second track to the first track for unhindered movement on said first track in said second direction.

2. A blocking device according to claim 1, wherein each retaining member comprises an inclined sliding surface having a predetermined length along which the engagement section will slide, and a step in the shape of a surface arranged at a sharp angle in relation to the sliding surface, said step connecting the top of one inclined sliding surface and the bottom of the next sliding surface, such that a saw-tooth configuration is created, and such that the engagement section of the leg will be retained from movement in one direction by said step.

3. A blocking device according to claim 1 wherein at least a part of a side surface facing the first track of each retaining member is arranged at a shallow angle in respect to the longitudinal axis of the device, such that the inclined sliding surface is narrowest in the end of the first travelling direction of the engagement section.

4. A blocking device according to claim 2 wherein the inclined sliding surface overlaps an adjacent inclined sliding surface, and that the inclined sliding surface tapers perpendicular to the longitudinal axis such that the top is narrower than the bottom of the sliding surface, whereby the step at the bottom is narrower than the adjacent sliding surface at their connection point.

5. A blocking device according to claim 1, claim 1 the leg member is pivotally fastened in the end opposite the engagement section, and that the first part comprising the at least one set of tracks has a corresponding circular configuration arranged at a distance, whereby the engagement section may engage the tracks.

6. A blocking device according to claim 1, wherein the width of the sliding guide perpendicular to the longitudinal axis at its widest section is at least as wide as the retaining members step.

7. A blocking device according to claim 1, wherein all parts of the device are made from a plastic material.

8. A blocking device according to claim 1, wherein one or both of the mutually displaceable parts are relatively biased, for example by spring means, such that when the device is not operating, the engagement section will be engaging a point on the sliding guide.

9. A manually operated inhalation device in which the dispensation of a medicament dose from a canister arranged in the device is activated by depressing a button or lever, which button or lever is further connected to a mechanically return blocking device where said device comprises two cooperating and mutually displaceable parts:
    a first part wherein parallel to a longitudinal axis at least one set of tracks comprising a first track and a second track is provided, and that the second track comprises one or more retaining members and a sliding guide arranged at one end of the second track;
    a second cooperating part wherein a leg member comprising an engagement section for engagement with the tracks provided on the first part is provided, and that said leg member is biased towards the first part and that the engagement section is adapted to travel in the direction of the longitudinal axis;
    and further that the retaining members allows the engagement section of the leg member to move in a first direction towards the sliding guide but blocks movement in an opposite second direction and that the engagement section of the leg member slides on the sliding guide, whereby the engagement section and thereby the leg member is directed from the second track to the first track.

10. Device according to claim 9, wherein the mutually displaceable parts are formed as integral parts of the device, such that the first or second part is integral with part of the button arrangement and the other part is integral with a non moving part of the device.

11. Device according to claim 9, wherein the engagement sections' travel between at least two adjacent retaining means or the retaining means and the sliding guide corresponds to the activation of one event, where an event may be the dispensation of a medicament dose and/or the input for a dose counting device.

12. Device according to claim 9, wherein the mechanical return blocking device is moulded at the same time as the device.

13. A blocking device according to claim 7, wherein the plastic material is a mouldable material.

14. A blocking device according to claim 7, wherein all parts of the device are made by an injection moulding process.

* * * * *